US007855164B1

(12) United States Patent
Reuber et al.

(10) Patent No.: US 7,855,164 B1
(45) Date of Patent: Dec. 21, 2010

(54) SCREENING METHODS EMPLOYING STRESS-RELATED PROMOTERS

(75) Inventors: Teresa Lynne Reuber, San Mateo, CA (US); Karen Century, Albany, CA (US); Joshua Armstrong, Richmond, CA (US)

(73) Assignee: Mendel Biotechnology, Inc., Hayward, CA (US)

( * ) Notice: Subject to any disclaimer, the term of this patent is extended or adjusted under 35 U.S.C. 154(b) by 364 days.

(21) Appl. No.: 11/356,722

(22) Filed: Feb. 17, 2006

Related U.S. Application Data

(60) Provisional application No. 60/655,745, filed on Feb. 22, 2005.

(51) Int. Cl.
*A01N 25/00* (2006.01)
*C12N 15/82* (2006.01)

(52) U.S. Cl. .................................. 504/116.1; 800/287
(58) Field of Classification Search ...................... None
See application file for complete search history.

(56) References Cited

U.S. PATENT DOCUMENTS 5,614,395 A * 3/1997 Ryals et al. ................... 435/6

FOREIGN PATENT DOCUMENTS

| WO | WO 00/29592 A2 | 5/2000 |
|---|---|---|
| WO | WO 00/55325 A2 | 9/2000 |
| WO | WO 01/98480 A2 | 12/2001 |
| WO | WO 02/16655 A2 | 2/2002 |
| WO | WO 02/22675 A2 | 3/2002 |
| WO | WO 02/072848 A2 | 9/2002 |
| WO | WO 02/081695 A2 | 10/2002 |
| WO | WO 03/000898 A1 | 1/2003 |

OTHER PUBLICATIONS

Montgomery et al (1993) PNAS 90:5939-5943).*
Vysotskaia et al, GenEmbl Database, Accession No. AC007591, May 19, 1999).*
Alonso et al. Five components of the ethylene-response pathway identified in a screen for weak ethylene-insensitive mutants in *Arabidopsis thaliana*. 2003. Proceedings of the National Academy of Sciences 100: 2992-2997.*
Nurkiyanova KM et al. Tagging potato leafroll virus with the jellyfish green fluorescent protein gene. J Gen Virol. Mar. 2000;81(Pt 3):617-26.*
Xu Yet al. Plant Defense Genes Are Synergistically Induced by Ethylene and Methyl Jasmonate. Plant Cell. Aug. 1994;6(8):1077-1085.*
Allen, Mark D. et al.; "A novel mode of DNA recognition by a β-sheet revealed by the solution structure of the GCC-box binding domain in complex with DNA"; 1998, *The EMBO Journal*, vol. 17, No. 18, pp. 5484-5496.
Cheong, Yong Hwa et al.; "BWMK1, a Rice Mitrogen-Activated Protein Kinase, Locates in the Nucleus and Mediates Pathogenesis-Related Gene Expression by Activation of a Transcription Factor"; 2003, *Plant Physiology*, vol. 132, pp. 1961-1972.
Gu, Young-Qiang et al.; "Pti4 is Induced by Ethylene and Salicylic Acid, and Its Product is Phosphorylated by the Pto Kinase"; 2000, *The Plant Cell*, vol. 12, pp. 771-785.
Hao, Dongyun et al.; "Unique Mode of GCC Box Recognition by the DNA-binding Domain of Ethylene-responsive Element-binding Factor (ERF Domain) in Plant"; 1998, *The Journal of Biological Chemistry*, vol. 273, No. 41, pp. 26857-26861.
Rushton, Paul J. et al.; "Synthetic Plant Promoters Containing Defined Regulatory Elements Provide Novel Insights into Pathogen- and Wound-Induced Signaling"; 2002, *The Plant Cell*, vol. 14, pp. 749-762.

* cited by examiner

*Primary Examiner*—Cynthia Collins
(74) *Attorney, Agent, or Firm*—Townsend and Townsend and Crew LLP

(57) ABSTRACT

The invention provides methods and compositions for identifying compounds that can enhance plant resistance to stress.

16 Claims, No Drawings

SEQUENCE LISTING

<160> NUMBER OF SEQ ID NOS: 9

<210> SEQ ID NO 1
<211> LENGTH: 706
<212> TYPE: DNA
<213> ORGANISM: Arabidopsis thaliana
<220> FEATURE:
<223> OTHER INFORMATION: exemplary transcription factor G28/G1792
      responsive promoter N1154 prAT3G62150

<400> SEQUENCE: 1
cgagtaagaa aattcattgg ctgcttgaaa gttgattcgt tacgtactga agtgtaatgt      60
gcacataata ataataataa aaattgtaaa gaaaaagtta tgagtcattc atttgccagc    120
taaaacaaat gcaagttgca tataagaaaa tcaatctgaa tttgatattt tgtctgcata    180
caatagaaat gcggttaatg gcaattgttt tatactgtat gaacaaagca aagtaaatgt    240
tgattagtca cactaaagtt tgaaagaaaa ctcgtttttt ggtactcttt tctttgtgaa    300
agaaaaagtt aggtgctaat aagactatcc gcagaacaga gaccagacca cttggcgtct    360
gacctgtcac gtcataacaa ggtcgttttt gacgactcta gtccttgttt ctggaagtag    420
gtcctgaact tccacttgaa tcaattcaat agacgtaaac gtcttaagag aagttcttga    480
aatcgaaaat ccactgcttc ttcttcaagt aatgaattag agtatattat atattcaacc    540
ctccacgatc cttgtttcct cggctactaa gaaaaggaag tgtatctgtg tttttcaggt    600
acatgcttct ctgttttttg ttgtccaata aagtttaagg tttcagtttt ctagatttta    660
aagtttggat ttttagcttt ggttttcttg ataggatcaa agaaca              706

<210> SEQ ID NO 2
<211> LENGTH: 2940
<212> TYPE: DNA
<213> ORGANISM: Arabidopsis thaliana
<220> FEATURE:
<223> OTHER INFORMATION: exemplary transcription factor G28/G1792
      responsive promoter N1155 prAT2G26560

<400> SEQUENCE: 2
ttcagaatag taagattaaa tcaaaaacaa aaaatttgtt tctttacaac taaaaacgat      60
ggtcatactc agtataagaa agaatttgtt tggaacttag tgtgattggt ttaaacgcag    120
ccaatgtgga taaaattaca ggagtataca aaagtggacg gttgcggttt taaatgttat    180
caagcagttt aaacgattgg tttagcggtt gaaaatatat gctttgtaaa aattatataa    240
ttgataaaat agcggatgtg agaacgatat aaagaaaaga aaatttgtta atcaagacgg    300
tcaaaaccaa aaagtttcgt ccttcgacta aatttttaata tgttatcggc ttcaattcga    360

```
agtgaaaacc ctagagaacc gaaagaaatc ataaactcta gtaattaatg ttctaaaatt      420
ataaaccaag aagggtgagg cccgtgaggg atagatggag aggagacgat cataaactaa      480
gaagagtgtt tataatgacg ttttgaattt cctcaatgaa accttctcac gttttgagaa      540
gtaggaaagc tttgcaggta cacgtggcat ttgagaatta gctatcagag tgtttgtcta      600
cgtggcatct tgagagagta gtttaccaat tgatgagatt gatggtttga gaaatctcaa      660 taaattttt ttcttaatag taaattttct taatttatat tttaaattaa attatcaaaa      720
gtggttagtt ttgcaaatca tctttcttga ttactcaata aatttctctc tcatcatatt      780
atatatatat atatatatat atatattaaa agcattcaaa ttcagaaagc aaaaattgaa      840
ataataattc tgctaatcgg ataattgtaa taagatgatg acgacgacga attaaggtgt      900
catttttggt acacattcac tcacttacta atcatattcg agattgatga tttgccgtat      960
caaaattatt cattgatttt gggttccaat tggtcttaat aaaatataac actttgcaaa     1020
tgttcaaaca tacaaatttg tatgaaatgc aagatctatt taattctaaa agtattacat     1080
taaatcaaat gtaaccggtg aaaagaata agaaaaaaaa acaaatgtaa ccatttcttt     1140
gcattatagt tttaaataga caaacttaaa tataattaca agtacaactc ttgattttat     1200
attgggatac agggataata gtataggttt gattggtgat tatcaaccgc agtttttttt     1260
cttgtcatca tttcaactgc aatttgggat ccaaaaaaca accaattgta aatacttcac     1320
attggtgggt gagaataaaa gtgtcaactt cattttccat ctctttatct atctaatcaa     1380
agaattctat caactcaatg atgaagaaac ttcaactttg catgtcttga gaaaaaaaga     1440
tattccagca tatcaatgtc gaatcatgtg atttgaaagg ataaaagtat attgctcaca     1500
aaatttctaa gtgttttcgc ggaaaataat aataatatat gcgattctat tcttttcttt     1560
gtcaattgtt ccaaaaatac attacgaaat tttacggtag agcaccacaa aaaaaaacga     1620
tattgctcaa taaacattc acatcaagaa gttattgctc aataaaaaaa aattgttttg     1680
taataaaaaa aacttttctt ttaatatatt tttattttttg taactgtgag gttcaaccat     1740
aaattttttt tttattaaaa ccaataaata tagcttaaat ctctttcaaa cttttttaca     1800
tatgtgacta accatcagtg acaattcgaa tttaatatta ctcacggtct agcagatgtg     1860
ttataaattt tgaaatcaat tataatttta caaattatat caaacttgga ctttgagtat     1920
gtctctattt gccttaaatg atcaaatatt acataaacaa aaaaacttga aattaaggtt     1980
attaataaat aatttaatat ttattttttga attttggtgg atttagaaag aataaaagta     2040 tttttttctgg gaaaatatgc atatttatat tatttgaatt gagtatagta aactaagggt     2100
gttaaatgaa aaacaaattg ttgtatgtac aaattgactt catttggtca atgaaagaaa     2160
gttgcagtgt tgggggataa gtattgagcg gcggctaaaa tactaaagat tttctaatat     2220
tgccataaaa gatattttt gtaactttct atttgtcacg gcactgattt tttcaaaact     2280
cccatgacac agctgtcttt accccataat atattgaacg taaagtaact tctttgacca     2340
attgaccatg cttagttgct tacgttgttt atacaaaaga ttcattgttg gaagtataag     2400
tagcagtaat attacatcgt aggttgtttt ctctcattaa catcgtctct aggtgactag     2460
aagaacgatc ctttgtgtgt gaactcgtga gcagaatcta aacgaaaatt atataaagct     2520
tagaattcat tagaaaaaag tgacatacca agaaacccga aatgggggaa gttaatttca     2580
tttgaacaaa aaaaaacatt gtagttttgt aataaaaggg ttgacatggt cttaatgtgg     2640
aagaagtaaa gaggctcacg aaaagtccat ggttgtctaca aaggaagaaa caagaaccaa     2700
tagaattaga gttcaaacca aaggacgaag tatgcaagtt aatttgacaa gctaatatcc     2760
```

| taagaatgaa gacatggtct aactttgaaa cagcagccac tagtgtccta taaatacata | 2820 |
| gagttcatta acctctcata atatctcaca atcaaagttc tatctcctca agtatcaata | 2880 |
| cattgatatc cattaaaaaa aagaaatatc aatacattgc tttgcttgtt ctgtaagatg | 2940 |

<210> SEQ ID NO 3
<211> LENGTH: 579
<212> TYPE: DNA
<213> ORGANISM: Arabidopsis thaliana
<220> FEATURE:
<223> OTHER INFORMATION: exemplary transcription factor G28/G1792
      responsive promoter N1156 prAT1G15125

<400> SEQUENCE: 3

| tttgcgctta ctacattttt ttgctacttg agtaattgca tggcctaata acaagatatg | 60 |
| ttgtgccttt ctttggtcca attgtcgtag acaatgcgtc aaacaaatca ttaggcttga | 120 |
| agtttcaata aagagagatt ttcaagcctc tgctattagg tggcctggta ctatggccat | 180 |
| tgattaggat ttcttagagc ttgccaaagt ttatgatcgg actaactctg aagcttattg | 240 |
| gtcttaaaaa gataactatc taatgatggc ggctacaaga agatatttc ttttaaaaaa | 300 |
| ttttgaaggt gaaagaaggt tgaatagtct tatggtgaaa tcacatgtga ctggaatgaa | 360 |
| gtgaagaact gtttagtgga gtgtgtgatg catgcagcag ccacttttga aggacagctt | 420 |
| ggactttaga gtgagagtga gatgtatggc ccgcggcggc tgcattagac tgaatcttat | 480 |
| ccttgacact ctacagcaat tatgtagatt ctcccatttg accctctatt taagggttag | 540 |
| caagtgtaat accagtccat acaataccat tacatagcc | 579 |

<210> SEQ ID NO 4
<211> LENGTH: 547
<212> TYPE: DNA
<213> ORGANISM: Arabidopsis thaliana
<220> FEATURE:
<223> OTHER INFORMATION: exemplary transcription factor G28/G1792
      responsive promoter N1159 prG179 (ATG01970)

<400> SEQUENCE: 4

| aagtgaatat gaatcaagtt tgaataacta tggagggatg aataatccat ggaatcaatg | 60 |
| attatatact tttgacaagt atagaagaaa gcaaagagcc aaaatagtca acaatctcaa | 120 |
| catcattcga gctcattgtt tattgaattc aatcaagttt ggtaggtgaa cctcaaatac | 180 |
| acgtgatatt ggatattatc ttggaaacct tgctaatcca aattgtaaat caaataagaa | 240 |
| aagaatgatt acctcagaga tctagatgca tattgattct tgaccaagaa atatgtttga | 300 |
| aatttgaatc cattgaacca aaatttgaag gagttgcata taataata taaatcagaa | 360 |
| tgatgtagcc gccacacctt tttgtttcca caaaactctt tttctgtgat ggatccgcta | 420 |
| atgtagccat attttcaata tatcacttt tctctggcat cttcgctacc gtgtacgtct | 480 |
| ctctttctct ccctcccctc cttggctttt ttcaagttcc caccataaac gcagagggag | 540 |
| ttaagaa | 547 |

<210> SEQ ID NO 5
<211> LENGTH: 207
<212> TYPE: DNA
<213> ORGANISM: Artificial Sequence
<220> FEATURE:
<223> OTHER INFORMATION: Description of Artificial Sequence:exemplary
      synthetic promoter box containing minimal promoter -continued

```
<400> SEQUENCE: 5
gatctcagcc gccaaagagg acccagaatg gatctcagcc gccaaagagg acccagaatg        60
gatctcagcc gccaaagagg acccagaatg gatctcagcc gccaaagagg acccagaatg       120
gatccgtcga ccgcaagacc cttcctctat ataaggaagt tcatttcatt tggagaggac       180
acgctcgacg gtgagctccg cggccgc                                           207

<210> SEQ ID NO 6
<211> LENGTH: 34
<212> TYPE: DNA
<213> ORGANISM: Arabidopsis thaliana
<220> FEATURE:
<223> OTHER INFORMATION: N1155 AT2G26560 G28/G1792 responsive promoter
      GCC box reverse orientation context

<400> SEQUENCE: 6
agtattgagc ggcggctaaa atactaaaga tttt                                    34

<210> SEQ ID NO 7
<211> LENGTH: 34
<212> TYPE: DNA
<213> ORGANISM: Arabidopsis thaliana
<220> FEATURE:
<223> OTHER INFORMATION: N1156 AT12G15125 G28/G1792 responsive promoter
      GCC box reverse orientation context

<400> SEQUENCE: 7
tatggcccgc ggcggctgca ttagactgaa tctt                                    34

<210> SEQ ID NO 8
<211> LENGTH: 34
<212> TYPE: DNA
<213> ORGANISM: Arabidopsis thaliana
<220> FEATURE:
<223> OTHER INFORMATION: N1156 AT1G15125 G28/G1792 responsive promoter
      GCC box reverse orientation context

<400> SEQUENCE: 8
atctaatgat ggcggctaca agaagatatt ttct                                    34

<210> SEQ ID NO 9
<211> LENGTH: 34
<212> TYPE: DNA
<213> ORGANISM: Arabidopsis thaliana
<220> FEATURE:
<223> OTHER INFORMATION: N1159 AT3G01970 G28/G1792 responsive promoter
      GCC box forward orientation context

<400> SEQUENCE: 9
agaatgatgt agccgccaca ccttttttgtt tcca                                   34
```

SCREENING METHODS EMPLOYING STRESS-RELATED PROMOTERS

CROSS-REFERENCE TO RELATED APPLICATIONS

This application claims benefit of U.S. Provisional Application No. 60/655,745, filed Feb. 22, 2005, which is herein incorporated by referenced.

BACKGROUND OF THE INVENTION

Enhancement of stress-resistance in plants, including tolerance to biotic and abiotic stresses, is desirable in many agricultural settings. Two transcription factors, G28 and G1792, mediate enhanced tolerance to multiple pathogens when overexpressed in plants, e.g., *Arabidopsis* (see, e.g., US Patent Publication No. 20030046723), as well as tolerance to abiotic stresses, including drought tolerance. Accordingly, genes that are regulated by these factors are of interest as targets to increase stress tolerance, including disease-resistance, drought tolerance, and chilling tolerance, in plants.

One method that can be employed to modulate G28 and G1792-regulated pathways that function in tolerance to stresses such as pathogens, drought and chilling is to upregulate expression of the transcription factors genetically. In some circumstances, it may be preferred to modulate these pathways using chemical means, rather than genetic means. Accordingly, there is a need to develop methods of identifying chemicals that modulate expression of the G28 and G1792-mediated stress tolerance pathways. The present invention provides advantages relative to other approaches in that compounds identified in accordance with the invention can be easily and quickly deployed.

BRIEF SUMMARY OF THE INVENTION

The invention provides methods and compositions for identifying chemicals that enhance stress tolerance in plants. The methods employ promoters that are modulated by the ERF family transcription factors G28 and G1792. Thus, in one aspect the invention provides a method of identifying a compound that enhances stress tolerance in plants, for example tolerance to pathogens, the method comprising contacting a candidate compound with a plant cell comprising a promoter operably linked to a reporter molecule, wherein the promoter comprises a minimum G28 or G1792-responsive promoter region of a promoter set forth in Table 1; detecting the level of expression of the reporter molecule, and selecting a compound that increases expression. In some embodiments, the promoter comprises the sequence, or a variant thereof, of the promoter sequences set forth in SEQ ID NOs: 1-4. The promoter can be either G28-responsive or G1792-responsive. In some embodiments, the promoter is both G28 and G1792-responsive.

The promoters for use in the invention often comprise a GCC box. The promoter can be a natural promoter, e.g., a promoter selected from the group listed in Table 1 or variant thereof, or an artificial promoter that comprises multiple copies, e.g., two to four, of the GCC box, e.g., a sequence such as the artificial promoter sequence set forth in SEQ ID NO:5.

In some embodiments, the plant cell is contacted with a plurality of candidate compounds. A compound that increases expression can then be identified from the pool of candidates by further testing using the methods described herein.

The reporter molecule can be any reporter molecule, e.g., a green fluorescent protein, or GUS.

The plant cell can be from any plant. In typical embodiments, the plant cell is from *Arabidopsis thaliana*. In other embodiments, the plant cell is a *Nicotiana benthamiana* plant cell.

The method can further comprise additional steps, e.g., steps to validate the compound. For example, in one embodiment, the method further comprises: contacting the candidate compound with a plant; assessing tolerance of the plant to pathogens; and selecting a compound that enhances tolerance to pathogens. In other embodiments, the method further comprises: contacting the candidate compound with a plant; assessing tolerance to an abiotic stress, such as drought or chilling; and selecting a compound that enhances tolerance to the abiotic stress.

In another aspect, the invention provides expression vectors and plant cells comprising the expression vectors. In some embodiments, an expression vector of the invention comprises a promoter operably linked to a nucleic acid encoding a reporter molecule, e.g., green fluorescent protein or GUS, wherein the promoter comprises a promoter, or variant thereof, set forth in Table 1. In some embodiments, the promoter is a minimum G28- or G1792-responsive promoter of one of the promoters listed in Table 1.

In another aspect, the invention provides compounds identified in accordance with the methods.

DETAILED DESCRIPTION OF THE INVENTION

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, and peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated.

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter can also optionally include distal elements, which can be located hundreds or thousands of base pairs from the start site of transcription, that participate in control of transcription.

In the context of this invention, a "G28 promoter" or a "G1792 promoter" refers to a promoter in these pathways, i.e., a promoter that is a target of the G28 and/or G1792 transcription factors.

A "minimum G28/G1792 responsive promoter" as used herein refers to a promoter region that is sufficient to mediate transcription in response to G28 and/or G1792. A minimum G28/G1792 promoter typically comprises the transcription factor binding site as well as additional sequences, i.e., a TATAA sequence, to support transcription of a gene that is operably linked to the promoter sequence.

The term "abiotic stress" refers to environmental conditions that reduce plant growth and viability, including, but not limited to, high salt concentration, high osmotic potential, drought, extremes of temperature (heat, chilling, freezing), extremes of light, and low nutrient levels (e.g., nitrogen, phosphorous, potassium, etc.).

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source.

The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

As used herein, an "expression cassette" is a nucleic acid construct, generated recombinantly or synthetically, with a series of specified nucleic acid elements that permit transcription of a particular nucleic acid in a target cell. The expression cassette can be incorporated into a plasmid, chromosome, mitochondrial DNA, plastid DNA, virus, or nucleic acid fragment. Typically, the expression cassette portion of the expression vector includes, among other sequences, a nucleic acid to be transcribed and a promoter.

The term "plant" includes whole plants, shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit (the mature ovary), plant tissue (e.g. vascular tissue, ground tissue, and the like) and cells (e.g. guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, bryophytes, and multicellular algae. It includes plants of a variety of ploidy levels, including aneuploid, polyploid, diploid, haploid and hemizygous. A "plant cell", e.g., for screening or other manipulatons, for the purposes of this invention is inclusive of "plant" as broadly defined.

The terms "isolated" "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. An isolated nucleic acid is separated from open reading frames that flank the gene and encode proteins other than the protein of interest. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The terms "identical" or percent "identity," in the context of two or more nucleic acids, refers to two or more sequences or subsequences that are the same or have a specified percentage of nucleotides that are the same (i.e., about 70% identity, preferably 75%, 80%, 85%, 90%, or 95% identity over a specified region, when compared and aligned for maximum correspondence over a comparison window, or designated region as measured using a BLAST or BLAST 2.0 sequence comparison algorithms with default parameters described below, or by manual alignment and visual inspection. Such sequences are then said to be "substantially identical." This definition also refers to the complement of a test sequence. Preferably, the identity exists over a region that is at least about 25 nucleotides in length, or more preferably over a region that is 50-100 nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1994-1999).

A preferred example of algorithms that are suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, optionally 10 times background hybridization. Exemplary stringent hybridization conditions can be as follows: 50% formamide, 5×SSC, and 1% SDS, incubating at 42° C., or, 5×SSC, 1% SDS, incubating at 65° C., with wash in 0.2×SSC, and 0.1% SDS at 65° C. Such washes can be performed for 5, 15, 30, 60, 120, or more minutes. For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

This invention relies on routine techniques in the field of recombinant genetics. Basic texts disclosing the general methods of use in this invention include Sambrook & Russell, *Molecular Cloning, A Laboratory Manual* (3rd Ed, 2001) and *Current Protocols in Molecular Biology* (Ausubel et al., eds., 1994-1999).

Introduction

The invention provides methods of screening chemical libraries to identify compounds that activate genes involved in stress resistance, e.g., resistance to pathogens and/or abiotic stress. The methods employ assays that evaluate activation mediated through promoters of disease and stress-responsive genes, e.g., promoters of the genes set forth in Table 1. Promoters for use in the invention are induced by the G28 and/or G1792 transcription factors.

Many genes in the G28 and G1792 pathways have been shown to contain the sequence AGCCGCC, termed the GCC box in their promoters (Hao, et al., *J. Biol. Chem*:273:26857-26861, 1998; Allen, et al., *EMBO J.* 17:5484-5496, 1998). Thus, promoters of the invention often comprise GCC boxes.

Selection of Promoters for Use in the Invention

Any number of G28 and/or G1792-responsive promoters can be used in practicing the invention. In some embodiments, the promoter is one of the promoters set forth in Table 1. The promoter need not be the exact sequence of Table 1. In some embodiments, the promoter may be longer, shorter, or comprise changes in the nucleotide sequence that do not result in loss of the ability to mediate activation through G28 and/or G1792.

Fragments or variants of a promoter for use in the invention are tested using known methodology. They are typically analyzed using reporter constructs in cellular assays in which the test fragments are linked to the coding sequence of a reporter gene. The G28 or G1792 transcription factor can be supplied, e.g., by expressing the transcription factor from an expression construct that is introduced into the cell, or by examining promoter response in a cell background in which the endogenous transcription factor is active, e.g., a plant that has been treated with a hormone such as ethylene or methyl jasmonate, or that has been exposed to a pathogen. Reporter activity is then compared to the level of activity of a reporter construct that comprises the reporter gene operably linked to control promoter, e.g., the longer promoter fragment, or a promoter fragment having the naturally occurring sequence. Promoters that demonstrate similar activity to the control promoter can then be used in the assays. Typically, such promoters show at least 50%, more often 70%, 80%, 90%, 100% or greater of the reporter activity of the control promoter construct.

In some embodiments, the promoter is a minimum G28 and/or G1792-responsive promoter of one of the promoters of the genes listed in Table 1. Such a minimum promoter fragment of a gene listed in Table 1 can be tested as outlined above. The minimum promoter can be shorter, or a variant, of a sequence shown in SEQ ID NOs:1-4, which correspond to promoter fragments listed in Table 1, or in some instance may be substantially the same sequence as set forth in one of SEQ ID NOs: 1-4.

Related promoters corresponding to the promoters of the loci listed in Table 1 can also be employed in the invention. Related promoters can be identified, for example, by analyzing the regulatory regions of corresponding genes in other species of plants, or of variants within the same species of plants. Such variants or related promoters can be identified, for example, by inspection of sequences upstream of homologous genes and testing the upstream sequences for G28- and/or G1792-responsiveness using assays as outlined above. Sequences corresponding to the genes, or related genes, noted in Table 1, can be found, e.g., in patent publications WO03000898, WO02081695, WO0216655, WO0222675, WO02072848, WO0198480, WO0055325, and U.S. Pat. No. 6,664,446. Related promoter sequences can also be identified by isolating a corresponding gene, e.g., by screening a library or PCR, from another plant species and testing the upstream sequence for G28- and/or G1792-responsiveness.

Synthetic Reporter Constructs

In some embodiments, the methods of the invention can employ artificial promoter constructs that are G28 and/or G1792-responsive. Such artificial promoter constructs typically comprise at least one GCC box, preferably two or more GCC boxes (see, e.g., Rushton et al., *The Plant Cell* 14:749-762, 2002) and a minimal promoter for activating transcription. In some embodiments, the synthetic promoter has four GCC boxes. An exemplary synthetic promoter is shown in SEQ ID NO:5.

The minimal promoter for use in synthetic constructs can be from any promoter. The minimal promoter supports basal transcription and typically comprises regulatory elements such as TATAA sequences. Exemplary minimal promoter regions can be from promoters such as the cauliflower mosaic virus (CaMV) 35S transcription initiation region, the 1'- or 2'-promoter derived from T-DNA of *Agrobacterium tumefaciens*, and other transcription initiation regions from various plant genes known to those of skill.

Synthetic promoters are tested to verify G28- and/or G1792-responsiveness, typically using reporter constructs, supra. The evaluation of promoter activity is typically performed in comparison to a known active promoter, e.g., a natural promoter such as a G28- and/or G1792-responsive promoter from a gene set forth in Table 1. Synthetic promoters for use in the invention generally have at least 50%, more often 70%, 80%, 90%, 100% or greater of the reporter activity, of the promoter construct that has the known G28 and/or G1792-responsive promoter.

Reporter Genes

Reporter genes suitable for use in the invention are known to those of skill in the art. Reporters include, but are not limited to, fluorescent proteins, such as green or red fluorescent proteins, or variants that produce a fluorescent color; β-glucuronidase (GUS); luciferase; chloramphenicol acetyltransferase; β-galactosidase; and alkaline phosphatase. Transcription of the sequences encoding the reporter gene can be determined using any method known in the art. In some embodiments, protein activity of the reporter gene is measured, e.g., using a fluorescent reader or other instrumentation appropriate to the reporter system. Products to assist in determination of reporter activity are commercially available.

Samples that are treated with a candidate compound, or pool of candidate compounds, are compared to control samples without the test compound to examine the extent of modulation. Control samples (untreated with activators are assigned a relative activity value. Activation is then achieved when the reporter activity value relative to the control is 110%, optionally 150%, 200-500%, or 1000-2000%. A positive control, e.g., a compound known to activate G28 and/or G1792, such as ethylene or methyl jasmonate, can also be employed in the screening assay.

In other embodiments endpoints other than reporter activity are assayed. For example, expression levels of the mRNA or protein can be measured to assess the effects of a test compound on reporter activation. In this instance, the amount of transcription of the reporter construct is measured by assessing the level of mRNA that encodes the reporter gene, or alternatively of the protein product. These assays can be performed using any methods known by those of skill in the art to be suitable. For example, mRNA expression can be detected using amplification-based methodologies, northern or dot blots, nuclease protection and the like. Polypeptide products can be identified using immunoassays.

Introduction of Reporter Constructs into Plants

G28/G1792-responsive expression constructs of the invention can be introduced into the desired plant host by a variety of conventional techniques. For example, the vector can be introduced directly into the plant cell using techniques such as electroporation, microinjection, and biolistic methods, such as particle bombardment. Alternatively, the constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria.

Microinjection techniques are known in the art and well described in the scientific and patent literature. The introduction of DNA constructs using polyethylene glycol precipitation is described, e.g., in Paszkowski et al. *Embo J.* 3:2717-2722 (1984). Electroporation techniques are described in Fromm et al. *Proc. Natl. Acad. Sci. USA* 82:5824 (1985). Biolistic transformation techniques are described in Klein et al. *Nature* 327:70-73 (1987).

*Agrobacterium tumefaciens*-mediated transformation techniques, including disarming and use of binary vectors, are well described in the scientific literature. See, for example Horsch et al. *Science* 233:496-498 (1984), and Fraley et al. *Proc. Natl. Acad. Sci.* USA 80:4803 (1983).

The host plant cells for screening reporter constructs can be from any plant, including both dicots and monocots. Typically, plant cells are from Nicotiana benthamiana or *Arabidopsis thaliana* or another plant that is routinely transformed and assayed in the art.

Other plants also can be used in the screening methods taught herein. These include cereals, for example, maize, sorghum, rice, wheat, barley, oats, rye, milo, flax, or gramma grass. Other plant genera include, but are not limited to, Cucurbita, Rosa, Vitis, Juglans, Gragaria, Lotus, Medicago, Onobrychis; Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Avena, Hordeum, Secale, Allium, and Triticum.

Following transformation of the reporter constructs into the plant cell, the transformed cell or plant tissue is selected or screened by conventional techniques. The transformed cell or plant tissue containing the reporter construct can then be regenerated, if desired, by known procedures. Additional methodology for the generation of plants comprising expression constructs for screening chemicals can be found in the art (see, e.g., U.S. Pat. No. 5,614,395).

Chemical Libraries

The compounds tested as modulators of G28 and G1792 pathways are chemical compounds. Essentially any chemical compound can be used as a G28 and/or G1792 promoter activator in the assays of the invention. Most often, compounds can be dissolved in aqueous or organic (e.g., DMSO-based) solutions. The assays are designed to screen large chemical libraries and usually include automating the assay steps, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods involve providing a combinatorial chemical library containing a large number of candidate compounds. Such "combinatorial chemical libraries" are then screened in one or more assays, as described herein, to identify those library members (particular chemical species or subclasses) that display activate one or more G28 and/or G1792 promoter activity. The compounds thus identified can serve as conventional "lead compounds" or can themselves be used as potential or actual agents for treating plants.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, small organic molecule libraries (see, e.g., U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; and the like). Other chemistries for generating chemical diversity libraries can also be used. Chemical diversity libraries are also commercially available, e.g., from such companies as 3-Dimensional Pharmaceuticals Inc., Albany Molecular Research Inc., Alchemia Pty. Ltd., Argonaut Technologies Inc., ArQule Inc, Biofocus plc, Array Biopharma Inc., Axys Pharmaceutical Inc., Cambridge Combinatorial Ltd., Charybdis Technologies Inc, ChemBridge Corp., CombiChem Inc., ComGenex Inc., Discovery Partners International Inc., Diversa Corp., EnzyMed Inc. Versicor, Gryphon Sciences Inc, Ixsys Inc., Kosan Biosciences Inc., Maxygen Inc., Molecumetics Ltd., Nanoscale Combinatorial Synthesis Inc., Ontogen Corp., Orchid Biocompter Inc., Oxford Asymmetry Ltd., Oxford Molecular Group plc, Panlabs Inc., Pharmacopeia Inc., Phytera Inc., ProtoGene Inc., Sphere Biosystems Inc., Symyx Technologies Inc., and Systems Integration Drug Discovery Co.

Often, chemical libraries that are screened in the methods of the invention comprise compounds with molecular weights between 150 and 600, an average cLogP value of 3 (range 0-9), an average number of H-bonding acceptors of 3.5 (range 0-9), an average number of H-bonding donors of 1 (range 0-4) and an average of 3 rotatable bonds (range 0-9). Such characteristics are typical of agrichemicals known in the art.

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries, are themselves commercially available (see, e.g., Chembridge, Inc., San Diego, Calif.; ComGenex, Princeton, N.J., Tripos, Inc., St. Louis, Mo., 3D Pharmaceuticals, Exton, Pa., Martek Biosciences, Columbia, Md., etc.).

High Throughput Assays

In the high throughput assays, it is possible to screen up to several thousand different candidate compounds in a single day. For example, each well of a microtiter plate can be used to run a separate assay against a selected candidate compound, or, if concentration or incubation time effects are to be observed, every 5-10 wells can test a single candidate compound. Further, pools of candidate compounds can also be tested where multiple compounds are included in a single test sample. If an activator is then identified, the chemicals included in the pool can be individually tested to identify an active compound.

Validation of Compounds

Embodiments of the invention include methods comprising further validation of compounds selected as outlined above. Candidates that activate one or more genes in the G28 or G1792 pathway can be evaluated to determine that the selected chemicals proffer enhanced resistance to stress, e.g., pathogens or abiotic stress.

Many disease-causing organisms can be used in validating the chemical compounds in methods analyzing resistance to pathogens. These include, but are not limited to fungi such as *Erysiphe cichoracearum* (powdery mildew), *Botrytis cinerea* (grey mold), or *Sclerotinia sclerotiorum* (white mold); oomycetes such as *Peronospora parasitica* (downy mildew)

or *Phytophthora infestans* (late blight); viruses such as turnip crinkle virus; or bacteria such as *Pseudomonas syringae*.

An exemplary assay for validating a compound can, e.g., evaluate resistance to a fungus such as powdery mildew. For example, resistance to *Botrytis cinerea* can be assayed by growing Arabidopsis seedlings axenically for 14 days, spraying the seedlings with a suspension of $10^4$ to $10^5$ *Botrytis spores*/ml, and monitoring disease symptoms over a period of 5-14 days. Another exemplary assay evaluates resistance to *Erysiphe cichoracearum*. For example, *Erysiphe cichoracearum* can be assayed by infecting soil-grown plants with conidia (asexual spores), using either a camel hair brush to infect individual leaves, or a settling tower (Adam & Somerville, *Plant J* 9:341-356, 1996; Reuber et al., *Plant J* 16:473-485, 1998) to distribute spores evenly over entire plants, and monitoring the level of fungal growth over 7-10 days.

Compounds can also be validated by evaluating tolerance to abiotic stress. Selected candidates can also be evaluated to determine that they confer enhanced abiotic stress tolerance, e.g., cold and drought tolerance, to treated plants. Abiotic stress assays can be performed using any number of methods known in the art. For example, tolerance to cold can be determined as follows. Sterile seeds are planted on 80% MS+Sucrose (freezing) plates and incubated at 22° C. in 24 hr light for 11 days. The freezing plates are then incubated at 4° C. for 30 minutes, iced and incubated at −9° C. to −11° C. for 20 hours. The plates are then thawed at room temperature and subsequently incubated in a 22° C. growth chamber at 24 hr light. The plates are evaluated after 5 days of incubation. The endpoints assessed for evaluation include, e.g., seedling vigor, bleaching, green leaves, etc. and new growth of rosette leaves. Plants treated with the compounds are compared to control plants.

Other assays, such as drought and salt tolerance can similarly be used to assess phenotype in response to abiotic stress. For example, drought tolerance can be measured using an assay in which seedlings are grown on media with or without a candidate compound. The seedlings are then desiccated, e.g., within a laminar flow hood in a two-stage process. The lids are first removed from the plates for 3 h with a 180° rotation at 1.5 h. The seedlings are subsequently removed from the plates and allowed to dehydrate on the plate lid for an additional 4 h. They are then transferred onto fresh media without test compound and returned to the growth chamber. The plates are evaluated after 4 days of recovery.

"Enhanced tolerance" or "improved tolerance" to stress, either abiotic stress or pathogens, is considered to be a change, relative to control plants, in an endpoint measurement where the direction of the change correlates with the ability to withstand abiotic stress. One of skill in the art understands that this change can be an increase or decrease, depending on the endpoint. For example, lower ion leakage exhibited by a plant treated with a candidate compound at a given cold temperature relative to the ion leakage observed in a control untreated plant is indicative of tolerance to cold temperatures. In other instances, e.g., drought tolerance, an improved tolerance can be reflected by an increase in the measured endpoint of treated plants relative to control. For example, such an endpoint may be survival in response to desiccation. In other embodiments, the endpoint may reflect susceptibility to pathogens, e.g., the amount of pathogen growth on a plant.

Compounds are selected that provide an enhanced ability, e.g., a statistically significant change in an endpoint that correlates with stress tolerance, to withstand stress from a pathogen and/or abiotic stress.

Treatment of Plants

Once chemical compounds are identified, they can be used to treat any plant to enhance stress resistance, e.g., disease resistance, including, vegetable, fruit, and orchard crops. Plants that can be treated include both monocots and dicots and in particular, agriculturally important plant species, including but not limited to, crops such as soybean, wheat, corn, potato, cotton, rice, oilseed rape (including canola), sunflower, alfalfa, sugarcane and turf; or fruits and vegetables, such as banana, blackberry, blueberry, strawberry, and raspberry, cantaloupe, carrot, cauliflower, coffee, cucumber, eggplant, grapes, honeydew, lettuce, mango, melon, onion, papaya, peas, peppers, pineapple, spinach, squash, sweet corn, tobacco, tomato, watermelon, rosaceous fruits (such as apple, peach, pear, cherry and plum) and vegetable brassicas (such as broccoli, cabbage, cauliflower, brussel sprouts and kohlrabi). Other crops, fruits and vegetables whose phenotype may be changed include barley, currant, avocado, citrus fruits such as oranges, lemons, grapefruit and tangerines, artichoke, cherries, nuts such as the walnut and peanut, endive, leek, roots, such as arrowroot, beet, cassaya, turnip, radish, yam, sweet potato and beans.

The selected chemicals can be formulated for treating plants as a liquid or a solid form. For example, in liquid formulations, the plants can be treated with a spray, in a drench application, a drip application, or through irrigation. Formulations are prepared using known methodology and may comprise other reagents conventionally employed in formulation of agricultural chemicals, e.g., emulsifying agents, surfactants, etc. Examples of formulations include emulsifiable concentrates, directly sprayable or dilutable solutions, dilute emulsions, wettable powders, soluble powders, dusts, granules or microcapsules. The methods of application, such as spraying, atomising, dusting, wetting, scattering or pouring, are selected in accordance with the desired application.

The chemical compounds can be used to enhance resistance to many pathogens, including, fungi, bacteria, nematodes, viruses or viroids, etc. Examples of pathogens in agriculturally important crops are listed, e.g., in U.S. Patent Publication No. 20040219675.

EXAMPLES

Table 1 lists genes that are targets of G28 and G1792. The locus is identified using The *Arabidopsis* Information Resource (TAIR) identifier. The promoter sequences (SEQ ID NOS:6-9) of the listed loci that comprise GCC boxes are indicated by the designation of the GCC box position in the promoter. The "forward" or "reverse" indicates the orientation of the GCC box.

Example 1

Primary Screening Assay

To use a given promoter in a primary screening assay, the promoter sequence is fused to a reporter gene such as GFP and transformed into a plant, for example Arabidopsis. Because the expression characteristics of a transgene can vary depending upon its insertion point in the genome, a number of independent transgenic plant lines (10-50) are screened to find a line with the best expression characteristics, e.g. low background expression and high levels of inducible reporter gene expression after appropriate treatment. Appropriate treatments for G28- or G1792-responsive promoters include treatments that induce the expression or activity of G28 or G1792, such as pathogen infection or treatment with hormones such as ethylene or methyl jasmonate. Once an appropriate transgenic line is chosen, experiments are conducted in the 96-well format to evaluate the media conditions for seedling growth in 96-well plates, and confirm the induction of the reporter gene under expected conditions. Ideally, a chemical treatment is identified that can serve as a positive control in a high throughput assay.

Example 2

Primary Screen

In one example of a primary screen, 1 µl each of a large number of chemicals (1:1 dilution from the purchased stock) from a library purchased from a commercial source is added to 96 well plate containing in each well 5-10 promoter::GFP Arabidopsis seeds. The volume of the media in each well is 250 µl and the final concentration of the chemical in each well is 28 µM. The seeds are allowed to germinate and grow in the medium containing the chemical for one week and the GFP signal is quantified in a 96 well fluorescent reader (DTX800 Beckman). The data are normalized based on negative controls in the same plate that are not treated with any chemicals. The fold-increase in expression level in wells containing an added chemical relative to the expression level in wells with no added chemical for lines transformed with G28-responsive or G1792-responsive promoters fused to GFP reflects the activity of the chemical for induction of the G28 or G1792 pathway.

All publications, accession numbers, patents, and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

TABLE 1

G28 and G1792 target genes

| Locus | Promoter ID | Fold change in shoots over-expressing G28 | Fold change in shoots over-expressing G1792 | GCC forward | GCC reverse | context |
|---|---|---|---|---|---|---|
| AT3G62150 | N1154 | 5.7 | | | | |
| AT2G26560 | N1155 | 5.6 | | | 742 | agtattgagcGGCGGCTaaaatactaaagatttt |
| AT1G15125 | N1156 | 4.9 | 2.8 | | 119, 306 | tatggcccgcGGCGGCTgcattagactgaatctt atctaatgatGGCGGCTacaagaagatattttct |
| AT3G01970 | N1159 | 4.7 | | 181 | | agaatgatgtAGCCGCCacaccttttgtttcca |

Exemplary Promoter Sequences for promoters set forth in Table 1:

SEQ ID NO:1 N1154 prAT3G62150 (−706 to −1)

CGAGTAAGAAAATTCATTGGCTGCTTGAAAGTTGATTCGTTACGTACTGA

AGTGTAATGTGCACATAATAATAATAATAAAAATTGTAAAGAAAAAGTTA

TGAGTCATTCATTTGCCAGCTAAAACAAATGCAAGTTGCATATAAGAAAA

TCAATCTGAATTTGATATTTTGTCTGCATACAATAGAAATGCGGTTAATG

GCAATTGTTTTATACTGTATGAACAAAGCAAAGTAAATGTTGATTAGTCA

CACTAAAGTTTGAAAGAAAACTCGTTTTTTGGTACTCTTTTCTTTGTGAA

AGAAAAAGTTAGGTGCTAATAAGACTATCCGCAGAACAGAGACCAGACCA

CTTGGCGTCTGACCTGTCACGTCATAACAAGGTCGTTTTTGACGACTCTA

GTCCTTGTTTCTGGAAGTAGGTCCTGAACTTCCACTTGAATCAATTCAAT

AGACGTAAACGTCTTAAGAGAAGTTCTTGAAATCGAAAATCCACTGCTTC

TTCTTCAAGTAATGAATTAGAGTATATTATATATTCAACCCTCCACGATC

CTTGTTTCCTCGGCTACTAAGAAAAGGAAGTGTATCTGTGTTTTTCAGGT

ACATGCTTCTCTGTTTTTTGTTGTCCAATAAAGTTTAAGGTTTCAGTTTT

CTAGATTTTAAAGTTTGGATTTTTAGCTTTGGTTTTCTTGATAGGATCAA

AGAACA

SEQ ID NO:2 N1155 prAT2G26560 (−2937 to +3)

```
TTCAGAATAGTAAGATTAAATCAAAAACAAAAAATTTGTTTCTTTACAAC
TAAAAACGATGGTCATACTCAGTATAAGAAAGAATTTGTTTGGAACTTAG
TGTGATTGGTTTAAACGCAGCCAATGTGGATAAAATTACAGGAGTATACA
AAAGTGGACGGTTGCGGTTTTAAATGTTATCAAGCAGTTTAAACGATTGG
TTTAGCGGTTGAAAATATATGCTTTGTAAAAATTATATAATTGATAAAAT
AGCGGATGTGAGAACGATATAAAGAAAAGAAAATTTGTTAATCAAGACGG
TCAAAACCAAAAAGTTTCGTCCTTCGACTAAATTTTAATATGTTATCGGC
TTCAATTCGAAGTGAAAACCCTAGAGAACCGAAAGAAATCATAAACTCTA
GTAATTAATGTTCTAAAATTATAAACCAAGAAGGGTGAGGCCCGTGAGGG
ATAGATGGAGAGGAGCGATCATAAACTAAGAAGAGTGTTTATAATGACG
TTTTGAATTTCCTCAATGAAACCTTCTCACGTTTTGAGAAGTAGGAAAGC
TTTGCAGGTACACGTGGCATTTGAGAATTAGCTATCAGAGTGTTTGTCTA
CGTGGCATCTTGAGAGAGTAGTTTACCAATTGATGAGATTGATGGTTTGA
GAAATCTCAATAAATTTTTTTCTTAATAGTAAATTTTCTTAATTTATAT
TTTAAATTAAATTATCAAAAGTGGTTAGTTTTGCAAATCATCTTTCTTGA
TTACTCAATAAATTTCTCTCTCATCATATTTATATATATATATATATAT
ATATATTAAAAGCATTCAAATTCAGAAAGCAAAAATTGAAATAATAATTC
TGCTAATCGGATAATTGTAATAAGATGATGACGACGACGAATTAAGGTGT
CATTTTTGGTACACATTCACTCACTTACTAATCATATTCGAGATTGATGA
TTTGCCGTATCAAAATTATTCATTGATTTTGGGTTCCAATTGGTCTTAAT
AAAATATAACACTTTGCAAATGTTCAAACATACAAATTTGTATGAAATGC
AAGATCTATTTAATTCTAAAAGTATTACATTAAATCAAATGTAACCGGTG
AAAAAGAATAAGAAAAAAAAAACAAATGTAACCATTTCTTTGCATTATAGT
TTTAAATAGACAAACTTAAATATAATTACAAGTACAACTCTTGATTTTAT
ATTGGGATACAGGGATAATAGTATAGGTTTGATTGGTGATTATCAACCGC
AGTTTTTTTCTTGTCATCATTTCAACTGCAATTTGGGATCCAAAAAACA
ACCAATTGTAAATACTTCACATTGGTGGGTGAGAATAAAAGTGTCAACTT
CATTTTCCATCTCTTTATCTATCTAATCAAAGAATTCTATCAACTCAATG
ATGAAGAAACTTCAACTTTGCATGTCTTGAGAAAAAAAGATATTCCAGCA
TATCAATGTCGAATCATGTGATTTGAAAGGATAAAAGTATATTGCTCACA
AAATTTCTAAGTGTTTTCGCGGAAAATAATAATAATATATGCGATTCTAT
TCTTTTCTTTGTCAATTGTTCCAAAAATACATTACGAAATTTTACGGTAG
AGCACCACAAAAAAAAACGATATTGCTCAATAAAACATTCACATCAAGAA
GTTATTGCTCAATAAAAAAAATTGTTTTGTAATAAAAAAAACTTTTCTT
TTAATATATTTTATTTTTGTAACTGTGAGGTTCAACCATAAATTTTTTT
TTTATTAAAACCAATAAATATAGCTTAAATCTCTTTCAAACTTTTTTACA
TATGTGACTAACCATCAGTGACAATTCGAATTTAATATTACTCACGGTCT
AGCAGATGTGTTATAAATTTTGAAATCAATTATATAATTTTACAAATTATAT
CAAACTTGGACTTTGAGTATGTCTCTATTTGCCTTAAATGATCAAATATT
ACATAAACAAAAAAACTTGAAATTAAGGTTATTAATAAATAATTTAATAT
TTATTTTTGAATTTTGGTGGATTTAGAAAGAATAAAAGTATTTTTTCTGG
GAAAATATGCATATTTATATTATTTGAATTGAGTATAGTAAACTAAGGGT
GTTAAATGAAAACAAATTGTTGTATGTACAAATTGACTTCATTTGGTCA
ATGAAAGAAAGTTGCAGTGTTGGGGGATAAGTATTGAGCGGCGGCTAAAA
TACTAAAGATTTTCTAATATTGCCATAAAAGATATTTTTTGTAACTTTCT
ATTTGTCACGGCACTGATTTTTTCAAAACTCCCATGACACAGCTGTCTTT
ACCCCATAATATATTGAACGTAAAGTAACTTCTTTGACCAATTGACCATG
CTTAGTTGCTTACGTTGTTTATACAAAAGATTCATTGTTGGAAGTATAAG
TAGCAGTAATATTACATCGTAGGTTGTTTTCTCTCATTAACATCGTCTCT
AGGTGACTAGAAGAACGATCCTTTGTGTGTGAACTCGTGAGCAGAATCTA
AACGAAAATTATATAAAGCTTAGAATTCATTAGAAAAAAGTGACATACCA
AGAAACCCGAAAATGGGGAAGTTAATTTCATTTGAACAAAAAAAAACATT
GTAGTTTTGTAATAAAAGGGTTGACATGGTCTTAATGTGGAAGAAGTAAA
GAGGCTCACGAAAAGTCCATGTTGTCTACAAAGGAAGAAACAAGAACCAA
TAGAATTAGAGTTCAAACCAAAGGACGAAGTATGCAAGTTAATTTGACAA
GCTAATATCCTAAGAATGAAGACATGGTCTAACTTTGAAACAGCAGCCAC
TAGTGTCCTATAAATACATAGAGTTCATTAACCTCTCATAATATCTCACA
ATCAAAGTTCTATCTCCTCAAGTATCAATACATTGATATCCATTAAAAAA
AAGAAATATCAATACATTGCTTTGCTTGTTCTGTAAGATG
```

SEQ ID NO:3 N1156 prAT1G15125 (−579 to −1)

```
TTTGCGCTTACTACATTTTTTTGCTACTTGAGTAATTGCATGGCCTAATA
ACAAGATATGTTGTGCCTTTCTTTGGTCCAATTGTCGTAGACAATGCGTC
AAACAAATCATTAGGCTTGAAGTTTCAATAAAGAGAGATTTTCAAGCCTC
TGCTATTAGGTGGCCTGGTACTATGGCCATTGATTAGGATTTCTTAGAGC
TTGCCAAAGTTTATGATCGGACTAACTCTGAAGCTTATTGGTCTTAAAAA
GATAACTATCTAATGATGGCGGCTACAAGAAGATATTTTCTTTTAAAAAA
TTTTGAAGGTGAAAGAAGGTTGAATAGTCTTATGGTGAAATCACATGTGA
CTGGAATGAAGTGAAGAACTGTTTAGTGGAGTGTGTGATGCATGCAGCAG
CCACTTTTGAAGGACAGCTTGGACTTTAGAGTGAGAGTGAGATGTATGGC
CCGCGGCGGCTGCATTAGACTGAATCTTATCCTTGACACTCTACAGCAAT
TATGTAGATTCTCCCATTTGACCCTCTATTTAAGGGTTAGCAAGTGTAAT
ACCAGTCCATACAATACCATTACATAGCC
```

SEQ ID NO:4 N1159 prG179 (At3g01970) (−547 to −1)

```
AAGTGAATATGAATCAAGTTTGAATAACTATGGAGGGATGAATAATCCAT
GGAATCAATGATTATATACTTTTGACAAGTATAGAAGAAAGCAAAGAGCC
AAAATAGTCAACAATCTCAACATCATTCGAGCTCATTGTTTATTGAATTC
AATCAAGTTTGGTAGGTGAACCTCAAATACACGTGATATTGGATATTATC
```

-continued

TTGGAAACCTTGCTAATCCAAATTGTAAATCAAATAAGAAAAGAATGATT

ACCTCAGAGATCTAGATGCATATTGATTCTTGACCAAGAAATATGTTTGA

AATTTGAATCCATTGAACCAAAATTTGAAGGAGTTGCATATATAATAATA

TAAATCAGAATGATGTAGCCGCCACACCTTTTTGTTTCCACAAAACTCTT

TTTCTGTGATGGATCCGCTAATGTAGCCATATTTTCAATATATATCACTT

TCTCTGGCATCTTCGCTACCGTGTACGTCTCTCTTTCTCTCCCTCCCCTC

CTTGGCTTTTTTCAAGTTCCCACCATAAACGCAGAGGGAGTTAAGAA

SEQ ID NO:5 synthetic promoter box containing minimal promoter

5  GATCTCAGCCGCCAAAGAGGACCCAGAATGGATCTCAGCCGCCAAAGAGG

ACCCAGAATGGATCTCAGCCGCCAAAGAGGACCCAGAATGGATCTCAGCC

GCCAAAGAGGACCCAGAATGGATCCGTCGACCGCAAGACCCTTCCTCTAT

10 ATAAGGAAGTTCATTTCATTTGGAGAGGACACGCTCGACGGTGAGCTCCG

CGGCCGC

---

What is claimed is:

1. A method of screening for a compound that enhances stress tolerance in plants, the method comprising contacting a candidate compound with a plant cell comprising a promoter operably linked to a reporter molecule, wherein the promoter comprises a minimum G28/G1792-responsive promoter region that (i) has at least 90% identity to SEQ ID NO:3 as determined with a BLASTN algorithm using as defaults a wordlength (W) of 11, an expectation (E) of 10, M=5, N=−4 and a comparison of both strands, and (ii) comprises the nucleotide sequence of the GCC boxes (GGCGGCT) set forth in SEQ ID NO:3;

detecting the level of expression of the reporter molecule, and selecting the compound that increases expression, thereby screening for a compound that enhances stress tolerance in plants.

2. The method of claim 1, wherein the promoter is both G28-responsive and G1792-responsive.

3. The method of claim 1, wherein the promoter is G28-responsive.

4. The method of claim 1, wherein the promoter is G1792-responsive.

5. The method of claim 1, wherein the promoter has at least 95% identity to SEQ ID NO:3 as determined with a BLASTN algorithm using as defaults a wordlength (W) of 11, an expectation (E) of 10, M=5, N=−4 and a comparison of both strands.

6. The method of claim 1, wherein the promoter comprises SEQ ID NO:3.

7. The method of claim 1, wherein a plurality of candidate compounds are contacted with a plant cell.

8. The method of claim 1, wherein the level of expression of the reporter molecule is detected by detecting an increase in reporter molecule activity.

9. The method of claim 1, wherein the reporter molecule is green fluorescent protein.

10. The method of claim 1, wherein the reporter molecule is β-glucuronidase (GUS).

11. The method of claim 1, wherein the plant cell is from *Nicotiana benthamiana*.

12. The method of claim 1, wherein the plant cell is from *Arabidopsis thaliana*.

13. The method of claim 1, further comprising:
contacting the candidate compound with a plant;
assessing tolerance of the plant to pathogens; and
selecting the compound that enhances tolerance to pathogens.

14. The method of claim 1, further comprising:
contacting the candidate compound with a plant;
assessing tolerance of the plant to an abiotic stress; and
selecting the compound that enhances abiotic stress tolerance.

15. The method of claim 14, wherein the abiotic stress is drought or water restriction.

16. The method of claim 14, wherein the abiotic stress is chilling.

* * * * *